United States Patent [19]

Yamamoto et al.

[11] Patent Number: 5,541,111
[45] Date of Patent: Jul. 30, 1996

[54] *LACTOBACILLUS HELVETICUS* MUTANTS HAVING LOW INCREASE IN ACIDITY OF LACTIC ACID DURING STORAGE

[75] Inventors: Naoyuki Yamamoto, Sagamihara; Yoshiko Masujima, Kashiwa; Toshiaki Takano, Kawasaki, all of Japan

[73] Assignee: The Calpis Food Industry Co., Ltd., Tokyo, Japan

[21] Appl. No.: 330,302

[22] Filed: Oct. 27, 1994

[30] Foreign Application Priority Data

Nov. 4, 1993 [JP] Japan .................................. 5-275791

[51] Int. Cl.$^6$ .............................. A23C 9/12; C12N 1/00; C12N 1/20
[52] U.S. Cl. .................... 435/252.9; 424/93.45; 426/34; 435/853
[58] Field of Search ................... 435/252.9, 853; 424/93.45; 426/34

[56] References Cited

U.S. PATENT DOCUMENTS 3,984,575  10/1976  Farr .................................... 426/61
4,839,281  6/1989  Gorbach et al. ...................... 435/34
5,179,020  1/1993  Herman et al. ...................... 435/252.9

FOREIGN PATENT DOCUMENTS 0113215  7/1984  European Pat. Off. .

OTHER PUBLICATIONS

Bergey's Manual, vol. 2, Exceprt p. 1208 © 1986.
AJ.T.C. Catalogue of Bacteria & Barteriophages, 18th ed, 1992, p. 173.

*Primary Examiner*—John W. Rollins
*Assistant Examiner*—Deborah K. Ware
*Attorney, Agent, or Firm*—Darby & Darby, P.C.

[57] ABSTRACT

Lactic acid bacteria of the genus Lactobacillus having the following specific properties: (1) an increased amount of acidity of lactic acid when storing a product cultured by the bacteria at 10° C. for two weeks being 0.5% or less; (2) an activity of cell membrane bound adenosine triphosphatase being 5 μmol·Pi/min/mg protein or less; and (3) the bacteria having neomycin resistance.

5 Claims, No Drawings

5,541,111

LACTOBACILLUS HELVETICUS MUTANTS HAVING LOW INCREASE IN ACIDITY OF LACTIC ACID DURING STORAGE

BACKGROUND OF THE INVENTION

This invention relates to a fermented milk product in which the increase in acidity in the low pH region and during storage at lower temperatures is inhibited, and novel lactic acid bacteria of the genus Lactobacillus that may be employed for the preparation of such fermented milk product.

The lactic acid bacteria of the genus Lactobacillus have long been known as a representative starter for preparation of fermented milk. The lactic acid bacteria of rod shape, such as the genus Lactobacillus produces lactic acid of higher acidity than that of the lactic acid bacteria of coccus such as the genus Lactococcus or the genos Stretococcus, while being frequently higher in its protease activity of decomposing milk protein. In particular, *Lactobacillus helveticus* exhibits strong protein-decomposing activity. The peptide generated by decomposition of milk protein by its extracellular protease has been reported to exhibit the inhibition activity against angiotensin converting enzyme (Hereinafter referred to as ACE) which is a substance responsible for increase in blood pressure. Similar activity may be noticed with the fermented milk by the *Lactobacillus helveticus*. These ACE inhibitory peptides have been confirmed to exhibit the activity in lowering the blood pressure with spontaneously hypertensive rats (SHR), as reported by Nakamura, Y. et al NIPPON NOGEI KAGAKU KAISHI, 67, 289, 1993.

However, *Lactobacillus helveticus* produces a large quantity of lactic acid during milk fermentation and hence is lowered significantly in pH. Besides, the acidity of lactic acid tends to be increased during storage at low temperature. Consequently, *Lactobacillus helveticus* is difficultly used for the preparation of yogurt, etc., such that it is scarcely used at present for yogurt-like fermented milk products.

In general, the increase in acidity during storage following the preparation of yogurt poses a serious problem. For suppressing such increase in acidity, various trials have been made such as inprovement of strains by mutation. However, desired mutant strains have not been produced because mutant strains low in growth activity tend to be separated.

Adenosine triphosphatase (Hereinafter referred to as ATPase) has so far been confirmed to be taking part in intracellular pH adjustment in the microorganisms. Although the extracellular pH of lactic acid bacteria is in an acidic range by the production of lactic acid as a final metabolite in the fermentation of lactic acid bacteria, the intracellular pH of the lactic acid bacteria is maintained in a neutral range by the action of ATPase. On the other hand, ATPase tends to be produced in an increasingly larger quantity with increase in the difference between the intracellular pH and the extracellular pH. Thus, it has been confirmed that, under the conditions in which such cell-wall barrier is destroyed in the acidic medium to eliminate the protonic concentration gradient, the microorganism cells cannot be proliferated (The Journal of Biological Chemistry, 261, 2.627–630, 1986, by Hiroshi Kobayashi, Takeshi Suzuki and Tsutomu Umemoto; and The Journal of Dairy Science, 74, 747–751, 1991, by Nancy L-Nannen and Robert W. Hutkins). While, these reports are directed to the relation between the extracellular pH and ATPase activity of the cells, there is no disclosure as to the final pH of a fermented product obtained by fermentation of the microorganisms.

Concerning neomycin resistance, the neomycin-resistant mutant strain *Escherichia coli* has been known to be devoid of ATPase activity (J. of Bacteriology, 116, 3. 1124–1129, 1973, by Barry P. Rosen). However, there is no disclosure as to lactic acid production.

SUMMARY OF THE INVENTION

It is an object of the present invention to provide lactic acid bacteria of the genus Lactobacillus which is a mutant strain having low increase in acidity of lactic acid during culturing and storage of th cultured product while maintaining characteristics of lactic acid bacteria of the genus Lactobacillus such that it exhibits substrate specificity against milk protein and strong proteolytic activity and produces the ACE inhibitory peptide in the fermented milk.

It is another object of the present invention to provide a fermented milk product in which increase in acidity of lactic acid is suppressed in the low pH range and during storage at lower temperatures.

The above and other objects of the present invention will become apparent from the following description.

The present invention provides lactic acid bacteria of the genus Lactobacillus having the following specific properties:

(1) an increased amount of acidity of lactic acid when storing a product cultured by the bacteria at 10° C. for two weeks being 0.5% or less;

(2) an activity of cell membrane bound adenosine triphosphatase being 5 μmol·Pi/min/mg protein or less; and (3) the bacteria having neomycin resistance.

The present invention also provides a fermented milk product produced by fermentation using the above-defined lactic acid bacteria.

PREFERRED EMBODIMENTS OF THE INVENTION

The present invention will be described in more detail hereinbelow.

The lactic acid bacteria of the genus Lactobacillus according to the present invention (hereinafter referred to simply as "lactic acid bacteria") is a mutant strain of the lactic acid bacteria of the genus Lactobacillus. Although the lactic acid bacteria of the present invention is not changed in the microbiological properties owned by the lactic acid bacteria of the parent strain and is not changed above all in intensity of the extracellular protease activity and substrate specificity, it exhibits characteristics distinct from the parent strain in the following three points, namely, (1) an increased amount of acidity of lactic acid when storing a product cultured by the bacteria at 10° C. for two weeks being 0.5% or less; (2) an activity of cell membrane bound adenosine triphosphatase being 5 μmol·Pi/min/mg protein or less; and (3) the bacteria having neomycin resistance.

It suffices if the increased amount of acidity of lactic acid when storing a product cultured by the bacteria at 10° C. for to weeks is 0.5% or less and preferably 0.4% or less, while there is no limitation to the increased amount of acidity of lactic acid under any other conditions. However, the final acidity of he lactic acid at the time of cultivation is preferably 0.5 to 1.2% and more preferably 0.6 to 1.0%, and when storing a product cultured by the bacteria at 10° C. for one week, the increase of acidity of lactic acid is preferably not higher than 0.4% and more preferably not higher than 0.2%.

Although the activity of cell membrane bound ATPase is changed with the pH in the culture medium, it is not higher than 5 mol·Pi/min/mg protein. The cell membrane bound ATPase activity can measured by the method of Neu, H. C & Heppel. L. A. J. Biol. Chem. 240. 3685 (1965), that is by extracting the protein under an osmotic shock, adding 40 μl of the extracted solution to 10 μl a of a solution (pH 6.5) of 250 mM of tris-hydrochloric acid, 25 mM of magnesium chloride, 25 mM of adenosine sodium triphosphate and 16.5 g/m bovine serum albumin (BSA), for reaction at 37° C. for one minute, adding 5 μl of 0.1N hydrochloric acid to the reaction solution to terminate the reaction, and subsequently measuring the concentration of the produced inorganic phosphoric acid using a reagent "P-TEST WAKO" produced by WAKO PURE CHEMICAL INDUSTRIES, LTD., and by the method proposed by Bradford (Anal. Biochem. 72, 284, 1976, by Bradford M. M.) in which the protein concentration in the extracted solution is measured.

The lactic acid bacteria exhibits neomycin resistance. It suffices if it is capable of being proliferated without extinction when cultured on a neomycin-containing culture medium.

There is no limitation to the lactic acid bacteria of the present invention if it exhibits bacteriological properties of the parent strain and also exhibits the specific properties (1) to (3) as mentioned above. A specific example of such bacteria is the lactic acid bacteria of the genus Lactobacillus deposited with the NATIONAL INSTITUTE OF BIOSCIENCE AND HUMAN TECHNOLOGY, AGENCY OF INDUSTRIAL SCIENCE AND TECHNOLOGY, as FERM-P13914 under the International Deposit No.BP-4835 (Hereinafter referred to as CPN4).

The bacteriological properties of CPN4 were analyzed by the method proposed by Mitsuoka (Journal of Medical Technology, 18.1163, 1974). By these analyses for identification, it could be confirmed that, while the bacteria CPN4 exhibited bacteriological properties similar to those of the parent strain *Lactobacillus helveticus* JCM 1004, it exhibited properties evidently different from those of the parent stain in point of neomycin resistance, low ATPase activity and low growth rate in the low pH range, so that it could be identified as being its pH-sensitive mutant strain. The specific bacteriological properties of the mutant strain are given in the following Table 1:

TABLE 1

I. Morphological Properties
1) Morphology; rod shape
2) Mobility; none
3) Spore Formation; none
4) Gram Stain; positive
II. Physiological Properties:
1) Catalase Production; negative
2) Indole Production; negative
3) Nitrate Reduction; negative
4) Aerobic Growth; facultative anaerobic
5) Formation of DL-lactic acid from glucose by homolactic fermentation without formation of gases
6) Formation of Acids from Carbohydrates;
glucose; +
maltose; −
Lactose; +
cellobiose; −
mannose; +
trehalose; −
fructose; +
melibiose; −
galactose; +
raffinose; −
sucrose; −
stachyose; −
mannitol; −
arabinose; −
sorbitol; −
xylose; −
esculin; −
rhamnose; −
salicin; −

7) Neomycin resistance; growth in 40 μg of neomycin/ml or less
8) ATPase activity; 5 μmol·Pi/min/mg protein or less The lactic acid bacteria of the present invention may be prepared by mutating the lactic acid bacteria of the genus Lactobacillus, i.e. the parent strain, by a method which will now be explained.

There is no limitation to the parent strain provided that it is of the genus Lactobacillus. Examples of such parent strains include lactic acid bacteria having high lactic acid producibility, such as *Lactobacillus helveticus* or *Lactobacillus delbuneckii* subsp. bulgaricus.

The lactic acid bacteria of the genus Lactobacillus are proliferatively cultured on a culture medium exhibiting high proliferation for each strain, such as Briggs Liver Broth, MRS culture medium, BL culture medium or GAM culture medium. The strains thus cultured are collected in the log phase. The innoculum size of the lactic acid bacteria in each culture medium is preferably about $1\times10^6$ cells/ml. For culturing, it is preferred that the culturing temperature be 30° to 45° C. and the culturing time period be 3 to 24 hours.

Since it is proposed by Barry (J. of Bacteriology, 116, 1124–1129, 1973, by Barry, P. R.) that screening from the neomycin resistant strains is effective for isolating the strains with low ATPase activity, the collected parent strains are inoculated on a proliferation agar medium containing 5 to 100 μg/ml of neomycin for selecting neomycin resistant strains in accordance with this proposal.

For inducing of the mutation effectively with the proposed method, the parent strains may be pre-treated by, for example UV irradiation or a chemical mutagen. For UV irradiation, it is preferred that the UV rays be not more than 500 nm in wavelength, the radiation time period be several seconds to 30 minutes and the irradiation distance be 10 to 30 cm. For effective selection of the mutant strains, it is preferred that viable bacteria in the log phase be suspended in the culture medium for proliferation and UV ray irradiation be conducted under the condition which will give the viability of 0.1 to 1.0%. For processing by the chemical mutagen, such as nitrosoguanidine (N-methyl-N'-nitro-nitrosoguanidine), ethyl methane sulfonic acid, methyl methane sulfonic acid or 5-bromouracil are employed as the chemical mutagen. If nitrosoguanidine, for example, is employed, viable bacteria in the log phase are suspended in the culture medium for proliferation having the pH value of 5.0 to 8.0, preferably 6.0 to 7.0, and processing is preferably carried out at the processing temperature of from room temperature to 50° C., above all, from 30° to 37° C., for a processing time of 10 to 60 minutes, above all, for 15 to 30 minutes with the nitrosoguanidine concentration of 30 to 1000 g/m, above all, 100 to 300 g/m.

After selecting the neomycin resistant strains, those strains showing low proliferation are discarded and those showing low proliferation only at pH of 4.5 or lower are selected. The selected strains showing low proliferation at the low pH range are cultured in a milk medium, such as skim milk medium, at 30 to 45° C. for 1 to 3 days, and those cell strains having the final pH higher than that of the parent strains, that is the cell strains having a low increase in the final acidity of lactic acid is selected. The mutant strains having the final pH following the cultivation at pH 3.4 to 3.8 are ultimately selected and cultured in a milk medium at e.g. 30 to 45° C. for 3 to 24 hours. The cell strains ultimately exhibiting the same bacteriological properties as the parent strains and exhibiting the properties (1) to (3) are selected as the lactic acid bacteria of the present invention.

There is no particular limitation to the fermented milk product of the present invention provided that the product has been processed by fermentation using the above-mentioned lactic acid bacteria. Examples of the fermented milk products include yogurt, lactic acid fermented beverage or cheese, which may be produced by the conventional methods. The fermented milk product may be produced by employing any of known lactic acid bacteria, such as *Streptococcus thermophilus*, *Lactococcus lactis* or *Bifidobacterium longim* in combination with the lactic acid bacteria of the invention. For preparing the fermented milk products, any of known methods for preparation may be employed, on the condition that the above-defined lactic acid bacteria are employed.

The lactic acid bacteria of the genus Lactobacillus of the present invention may be employed for the preparation of fermented milk products, such as yogurt, in which it is possible to suppress the increase in the acidity of lactic acid on prolonged storage at lower temperatures. The fermented milk product of the present invention, employing the above-defined lactic acid bacteria, exhibits the antihypertensive activty, while maintaining the flavor peculiar to the product directly following the end of fermentation, in addition to exhibiting the properties of suppressing the increase in the acidity of lactic acid on prolonged storage at lower temperatures.

EXAMPLES OF THE INVENTION

The present invention will be explained with reference to Examples which are given for illustration only and are not intended for limiting the invention.

Example 1

Isolation of Mutant Strains $1\times10^6$ cells/ml of *Lactobacillus helveticus* JCM-1003, referred to hereinafter as the parent strain, were inoculated in the Briggs liver broth, and cultured at 37° C. for 20 hours. The cells were re-cultured in a new culture medium of the same type at 37° C. for 6 hours and the bacteria in the log phase were collected and irradiated with UV rays using a 15 W UV lamp for the irradiation time of 30 seconds at the irradiation distance of 20 cm. The bacteria were then inoculated on the Briggs agar culture medium containing 5 μg/ml of neomycin so that the viable bacteria were equal to $1\times10^6$ cells, and were cultured at 37° C. for two days. Fifty strains each capable of forming a larger colony were selected and replicated on a Briggs agar media adjusted to pH of 6.5 and 4.5. Fifteen strains showing the proliferation comparable to that of the parent strain on the culture medium of pH 6.5 and showing the proliferation lower than that of the parent strain on the culture medium of pH of 4.5 were selected and inoculated on a 9% skim milk. The culturing was continued at 37° C. for three days and the final pH values of the cultured strains were compared to those of the parent strain. The sole strain, referred to hereinafter as CPN4, having a high final pH as compared to that of the parent strain was selected. The mutant strain CPN4 and the parent strain were cultured for three days and measurement was made of the final pH and turbidity (absorbance at 590 nm). The results are shown in the following Table 2.

TABLE 2

| Strains | Final pH | Turbidity (O.D. 590 nm) |
| --- | --- | --- |
| L. helveticus JCM1003 | 3.23 | 3.58 |
| L. helveticus CPN4 | 3.64 | 2.54 |

Measurement of Cell Membrane Bound ATPase Activity

Nine strains of the *Lactobacillus helveticus* were cultured in a Briggs culture medium, pH 5.0, at 37° C. for 6 hours. From each cell, protein was extracted under the osmotic shock in accordance with the Neu's method (J. Biol. Chem. 240 3685, 1965, by Neu, H. C. & Heppel. L. A.). 40 μl of the extracted solution was added to 10 μl of a solution containing 250 mM tris-hydrochloric acid, pH 6.5, 25 mM of magnesium chloride, 25 mM of adenosine sodium triphosphate and 16.5 μg/ml of bovine serum albumin (BSA) and the resulting mixture was reacted at 37° C. for 10 minutes. The reaction was terminated by adding 5 μl of 0.1N hydrochloric acid to the reaction mass. The concentration of the produced inorganic phosphoric acid was measured using "P-TEST WAKO", a reagent manufactured by WAKO PURE CHEMICAL INDUSTRIES, LTD. The protein concentration in the extracted solution was measured by the Bradford's method (Anal. Biochem., 72 284, 1976, by Bradford M. M.). The ATPase activity was measured under the above-mentioned conditions and represented in terms of the amount yielded of the inorganic phosphoric acid by a unit amount of protein containing enzyme (mol·Pi/min/mg protein) (Table 3). The neomycin resistance of each strain was found by measuring the minimum growth inhibition concentration. The results are shown in the following Table 3.

TABLE 3

| Strains | ATPase activity (pmol · Pi/min/mg protein) | Neomycin resistance (minimum inhibition concentration μg/ml) |
| --- | --- | --- |
| L. helveticus CPN4 | 3.6 | 40 |
| L. helveticus JCM1003 | 22.0 | 10 |
| L. helveticus CP611 | 17.7 | 10 |
| L. helveticus CP615 | 15.6 | 10 |
| L. helveticus JCM1120 | 12.0 | 5 |
| L. helveticus JCM1004 | 13.1 | 10 |
| L. helveticus JCM1006 | 16.8 | 10 |
| L. helveticus JCM1007 | 15.2 | 5 |
| L. helveticus JCM1008 | 14.4 | 5 |

From the results of Table 3, it was confirmed that the parent strain JCM-1003 and other seven strains showed high levels of ATPase activity. However, the CPN4 strain showed ATPase activity lower than that of the parent strains.

The CPN4 strain and the parent strains were again cultured in a 9% skim milk at 37° C. for 30 hours, and measurement was made in accordance with the following method, as to whether or not the ACE inhibition activity and the peptide quantity of these mutant strains in the fermented milk were on the same order of magnitude as those of the parent strains. For reference, the extracellular protease activity of each strain was also measured and the final pH value was checked again. These results of measurement are shown in Table 4.

Measurement of ACE Inhibition Activity in Fermented Milk

Measurement of the ACE inhibition activity was conducted in accordance with the method by Cushman and Cheung (Pharmacol., 20 1637, 1971, by Cushman D. W. & Cheung H. S.). Each fermented milk sample was centrifuged at 15000 rpm for five minutes, to produce a supernatant (whey), which was then adjusted to a neutral pH using a 1N sodium hydroxide solution. 80 µl of the supernatant was transferred to a test tube, to which was added 0.2 ml of hippuryl histidyl leucine (Hip-His-Leu produced by SIGMA CHEMICAL CO.) adjusted to 5 mM with a 0.1 M boric acid buffer containing 0.3 M NaCl pH 8.3 as a substrate. 20 µl of an enzyme solution (0.1 unit/ml, produced by SIGMA CHEMICAL CO.) was added to the reaction system and the reaction was carried out at 37° C. for 30 minutes. 250 µl of 1N hydrochloric acid was then added to the reaction system to terminate the reaction. 1.7 m of ethyl acetate was added to the reaction system and stirred for about 20 seconds. The reaction system was centrifuged at 3000 rpm for 10 minutes in order to recover 1.4 m of an ethyl acetate layer. The solvent was then removed by heating at 120° C. for 40 minutes. After removing the solvent, 1 m of distilled water was added and, after stirring for about 20 seconds, absorbance at 228 nm of the extracted hippuric acid was measured. 1 unit of the enzyme activity was calculated by the following equation as an amount which gave 50% inhibition of the ACE activity:

$$\text{Enzyme quantity (1 unit)} = [(A-B)/(A-C)] \times 100 \times 1/50$$

where A is the absorbance (228 nm) not containing the sample, B is the absorbance (228 nm) admixed with the sample and C is the absorbance (228 nm) not admixed with the enzyme nor the sample.

The peptide quantity was determined in accordance with the OPA method (J. of Dairy Science, 66 1219, 1983, by Charch F. C. et al.). The standard curve was prepared using a trypsin digested product of casein as a standard.

Measurement of Extracellular Protease Activity

The extracellular protease activity was measured in accordance with the method by Yamamoto et al. (J. of Biochem. 114, 740, 1993, by Yamamoto et al.), based upon the method by Twining S. (Anal. Biochem. 143 3410, by Twining. S.). That is, each strain was cultured by maintaining at pH 6.0 in a 9% skim milk and bacteria thus produced were collected in the mid-log phase. Sodium citrate was added so that the final concentration was 1% to render the milk culture medium to be transparent followed by centrifugal separation at 5000 rpm for 10 minutes to collect the bacteria. The bacteria were washed with 50 mM β-glycerophosphoric acid and then suspended in a 50 mM tris-hydrochloric acid buffer (pH 7.8) and measurement was made of the enzymatic activity of the bacterial cell surface. 30 µl of the liquid suspension of bacterial cell was added to 20 µl of 0.4% fluoresceine-isothiocyanate-casein produced by SIGMA CHEMICAL CO. After incubation at 42° C. for one hour, 120 µl of a 5% trichloroacetic acid solution was added to the reaction system. After allowed to stand for about 20 minutes at room temperature, the reaction system was centrifuged at 15000 rpm for ten minutes. 60 µl of the supernatant was added to 3 ml of a 500 mM tris-hydrochloric acid buffer (pH 7.8) and fluorometry was carried out of the reaction mass. For fluorometry, measurement was made of the fluorescence of 525 nm produced at an excitation wavelength of 490 nm.

As for the enzymatic activity, the amount of enzyme corresponding to 1% intensity of fluorescence of total substrate was defined as being 1 unit. The CPN4 strain exhibited extracellular protease activity comparable to that of the parent strain. Similar values were obtained of the peptide quantity and the ACE inhibition activity. However, the final pH was again confirmed to be higher than that of the parent strain, Consequential, only the CPN4 strain showing the ACE inhibition activity in its fermented milk comparable to that of the parent strain and having the final pH higher than that of the parent strain were selected as being satisfactory.

TABLE 4

| Strains | Final pH | Peptide quantity (%) | ACE inhibition activity (U/ml) | Protease activity (U/O.D. 590 nm) |
|---|---|---|---|---|
| L. helveticus JCM1003 | 3.24 | 0.24 | 32.3 | 101 |
| L. helveticus CPN4 | 3.62 | 0.23 | 28.6 | 103 |

Low Temperature Storage Test

A low temperature storage test of the mutant strain CPN4 strain was then conducted at 10° C. The parent strain and the CPN4 strain were cultured in milk at 37° C. and at a time point when the amount of the produced lactic acid reached 0.6%, the fermented milk was cooled and stored at 10° C. In one week and in two weeks after storage, the pH value, the acidity of lactic acid (%), the ACE inhibition activity and the peptide quantity were measured. The results are shown in Table 5.

TABLE 5

| Strains | Storage period | pH | Acidity (%) | ACE inhibition activity (U/ml) | Peptide quantity (%) |
|---|---|---|---|---|---|
| L. helveticus JCM1003 | Start of storage | 4.3 | 0.68 | 19.2 | 0.14 |
| | One week | 4.1 | 1.12 | 20.2 | 0.17 |
| | Two weeks | 3.7 | 1.27 | 26.2 | 0.17 |
| L. helveticus CPN4 | Start of storage | 4.3 | 0.68 | 17.7 | 0.16 |
| | One week | 4.2 | 0.83 | 18.5 | 0.19 |
| | Two weeks | 4.1 | 0.95 | 23.3 | 0.20 |

It is seen from the results of Table 5 that the fermented milk of the CPN4 strain showed no significant difference from that of the parent strain in the peptide quantity and in ACE inhibition activity. With the parent strain, the increase in the acidity of lactic acid and consequent lowering of the pH value were noticed. However, with the CPN4 strain, no significant change in the acidity of lactic acid was noticed during the storage period. The pH value of the fermented milk of the CPN4 strain was changed by 0.2 during storage for two weeks, while the acidity was increased by 0.27% during the storage period, indicating significant suppression of the increase in the acidic taste.

Antihypertensive Effect of the Fermented Milk on Spontaneously Hypertensive Rat Using the mutant strain CPN4 produced as described above, yogurt (corresponding to the culture in milk stored at 10° C. for one week in the above-described low temperature storage test) was prepared, and orally administered by a stomachic sonde to spontaneously hypertensive rats furnished by CHARLES RIBER JAPAN INC. in order to measure the vasodepression value. As a control, milk set to the same acidity with lactic acid was employed. Each of 6 ml/kg of fermented milk and no-fermented milk (control) was forecedly administered, respectively to male rats of 18 weeks of age (5 rats per group) and blood pressure was measured after 6 hours. For measuring the blood pressure, the systolic blood pressure was found by the tail-cuff method, using an apparatus "SOFTRON BP-98A" produced by SOFTRON CO. LTD. The results are shown in Table 6.

TABLE 6

| Samples | Change in Systolic Blood pressure after six hours |
|---|---|
| Non-fermented milk | −2.8 ± 4.5 mmHg |
| CPN4 fermented milk | −25.4 ± 12.5 mmHg |

Vasodepression by CPN4 femented milk is significant for p<0.01 with respect to that by non-fermented milk.

From the results of Table 6, it was found that the non-fermented milk showed no antihypertensive effect on the spontaneously hypertensive rats, while the fermented milk by the CPN4 strain showed strong antihypertensive effect on the same rats.

Example 2

To $1 \times 10^6$ cells/ml of the CPN4 strain produced in Example 1 were added *Streptococcus thermophilus* ATCC-144885 or ATCC-19258 so that each resulting mass was $1 \times 10^5$ cells/ml, and each resulting product was mixed and cultured at 37° C. for hours in the milk culture medium. The two cultured products were compared with each cultured product prepared using each of the parent strain, CPN4, *Streptococcus thermophilus* ATCC-144885 and *Streptococcus thermophilus* ATCC19258, respectively as to the acidity of lactic acid, pH, peptide quantity and ACE inhibition activity. The results are shown in Table 7.

TABLE 7

| Strains | Final pH | Acidity (%) | ACE inhibition activity (U/ml) | Peptide quantity (%) |
|---|---|---|---|---|
| L. helveticis JCM1003 | 3.5 | 2.1 | 29.0 | 0.19 |
| L. heleveticis CPN4 | 3.7 | 1.7 | 27.8 | 0.26 |
| S. thermophilis ATTC-144885 | 4.5 | 0.7 | 5.0 | 0.06 |
| S. thermophilis ATTC-19258 | 4.3 | 0.9 | 3.8 | 0.06 |
| L. helveticis CPN4 + S. thermophilis ATTC-144885 | 3.9 | 1.2 | 15.0 | 0.19 |
| L. helveticis CPN4 + S. thermophilis ATTC-19258 | 3.9 | 1.2 | 17.3 | 0.16 |

It is seen from the results of Table 7 that while the fermented milk of the parent strain was low in final pH and the highest in the acidity, the fermented milk of the CPN4 strain was higher than that of the parent strain in the final pH, and was also low in the acidity. On the other hand, the fermented milk of the Streptococcus thermophilus ATCC-144885 or ATCC-19258 fermented alone, showed only negligible increase in the acidity, while being low in the peptide quantity and low in the ACE inhibition activity. If these strains were used together with the CPN4 strain, the ACE inhibition activity was noticed in each of the strains, while the increase in the acidity was low. Taste was added by such mixed culturing as compared to that of the *Lactobacillus helveticus* as used alone.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. *Lactobacillus helveticus* mutants induced by a mutagen, and having the following specific properties:
   (1) an increase in acidity of 0.5% or less, said acidity resulting from an increase in lactic acid when storing a product cultured by the bacteria at 10° C. for two weeks;
   (2) an activity of cell membrane bound adenosine triphosphatase being 5 μ mol Pi/min/mg protein or less; and
   (3) the bacteria having neomycin resistance.

2. *Lactobacillus helveticus* mutants as claimed in claim 1 wherein total acidity resulting from lactic acid of the product after the storage ranges from 0.5 to 1.2%.

3. *Lactobacillus helveticus* mutants as claimed in claim 1 wherein the lactic acid bacteria are proliferated without extinction after culturing the lactic acid bacteria in a neomycin-containing culture medium.

4. *Lactobacillus helveticus* mutants as claimed in claim 1 wherein said bacteria have the following bacteriological properties:
   I. Morphological Properties
   1 ) Morphology; rod shape
   2) Mobility; none
   3) Spore Formation; none
   4) Gram Stain; positive
   II. Physiological Properties:
   1) Catalase Production; negative
   2) Indole Production; negative
   3) Nitrate Reduction; negative
   4) Aerobic Growth; facultative anaerobic
   5) Formation of DL-lactic Acid from glucose by homolactic fermentation without formation of gases
   6) Formation of Acids from Carbohydrates;
   glucose; +
   maltose; −
   lactose; +
   cellobiose; −
   mannose; +
   trehalose; −
   fructose; +
   melibiose; −
   galactose; +
   raffinose; −
   sucrose; −
   stachyose; −
   mannitol; −
   arabinose; −
   sorbitol; −
   xylose; −
   esculin; −
   rhamnose; −
   salicin; −
   7) Neomycin resistance; growth in 40 μg of neomycin/ml or less
   8) ATPase activity; 5 μmol·Pi/min/mg protein or less.

5. *Lactobacillus helveticus* mutants as claimed in claim 1 wherein said mutagen is selected from the group consisting of UV irradiation and a chemical mutagen.

* * * * *